(12) United States Patent
Pfeiffer et al.

(10) Patent No.: US 7,259,181 B2
(45) Date of Patent: Aug. 21, 2007

(54) β CRYSTALLINE FORM OF PERINDOPRIL TERT-BUTYLAMINE SALT

(75) Inventors: Bruno Pfeiffer, Saint Leu la Foret (FR); Yves-Michel Ginot, Orleans (FR); Gérard Coquerel, Boos (FR); Stéphane Beilles, Dijon (FR)

(73) Assignee: Les Laboratoires Servier, Courbevoie Cedex (FR)

( * ) Notice: Subject to any disclaimer, the term of this patent is extended or adjusted under 35 U.S.C. 154(b) by 0 days.

(21) Appl. No.: 11/052,489

(22) Filed: Feb. 4, 2005

(65) Prior Publication Data
US 2005/0203165 A1  Sep. 15, 2005

Related U.S. Application Data

(63) Continuation of application No. 10/312,902, filed as application No. PCT/FR01/02168 on Jul. 6, 2001, now abandoned.

(30) Foreign Application Priority Data
Jul. 6, 2000 (FR) .................... 00 08792

(51) Int. Cl.
*A61K 31/404* (2006.01)
*C07D 209/34* (2006.01)

(52) U.S. Cl. ...................... 514/412; 548/452
(58) Field of Classification Search ................ 548/452; 514/412
See application file for complete search history.

(56) References Cited

U.S. PATENT DOCUMENTS

| 4,914,214 | A * | 4/1990 | Vincent et al. | 548/492 |
| 6,653,336 | B1 * | 11/2003 | Guez et al. | 514/410 |

| 2004/0248817 | A1 * | 12/2004 | Pfeiffer et al. | 514/19 |
| 2005/0059609 | A1 * | 3/2005 | Pfeiffer et al. | 514/19 |

FOREIGN PATENT DOCUMENTS

| EP | 0308341 | 3/1989 |
| FR | 2771010 | 5/1999 |

OTHER PUBLICATIONS

Brittain "polymorphism in pharmaceutical solids" marcel Dekker, p. 1,2, 178-179, 185, 219 and 236 (1999).*
US Pharmacopia #23, national formulary #18, p. 1843-1844 (1995).*
A. Maureen Rouhi, Chemical & Engineering News, Feb. 24, 2003, pp. 32-35.*
Brittain "Polymorphism in Pharmaceutical Solids" Marcel Dekker, p. 332, 334, 335, 338-341, (1999).*

* cited by examiner

*Primary Examiner*—Rebecca Anderson
(74) *Attorney, Agent, or Firm*—Hueschen and Sage

(57) ABSTRACT

A β crystalline form of the compound of formula (I):

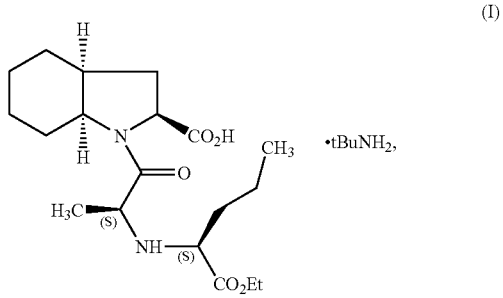

characterized by its powder X-ray diffraction data.

Medicinal products containing the same which are useful as inhibitors of angiotensin I converting enzyme.

1 Claim, No Drawings

β CRYSTALLINE FORM OF PERINDOPRIL TERT-BUTYLAMINE SALT

The present invention relates to a new β crystalline form of perindopril tert-butylamine salt of formula (I):

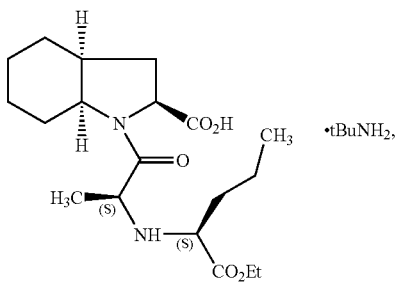

BACKGROUND OF THE INVENTION

Perindopril and its pharmaceutically acceptable salts, and more especially its tert-butylamine salt, have valuable pharmacological properties.

Their principal property is that of inhibiting angiotensin I converting enzyme (or kininase II), which prevents, on the one hand, conversion of the decapeptide angiotensin I to the octapeptide angiotensin II (a vasoconstrictor) and, on the other hand, degradation of bradykinin (a vasodilator) to an inactive peptide.

Those two actions contribute to the beneficial effects of perindopril in cardiovascular diseases, more especially in arterial hypertension and heart failure.

Perindopril, its preparation and its use in therapeutics have been described in European Patent specification EP 0 049 658.

In view of the pharmaceutical value of this compound, it has been of prime importance to obtain it with excellent purity. It has also been important to be able to synthesise it by means of a process that can readily be converted to the industrial scale, especially in a form that allows rapid filtration and drying. Finally, that form had to be perfectly reproducible, easily formulated and sufficiently stable to allow its storage for long periods without particular requirements for temperature, light, humidity or oxygen level.

DESCRIPTION OF THE PRIOR ART

The patent specification EP 0 308 341 (equivalent to U.S. Pat. No. 4,914,214, the subject matter of which is hereby incorporated by reference) describes an industrial synthesis process for perindopril. However, that document does not specify the conditions for obtaining perindopril in a form that exhibits those characteristics in a reproducible manner.

The Applicant has now found that a particular salt of perindopril, the tert-butylamine salt, can be obtained in a well defined, perfectly reproducible crystalline form that especially exhibits valuable characteristics for formulation.

DETAILED DESCRIPTION OF THE INVENTION

More specifically, the present invention relates to the β crystalline form of the compound of formula (I), characterized by the following powder X-ray diffraction diagram, measured using a Siemens D5005 diffractometer (copper anticathode) and expressed in terms of inter-planar distance d, Bragg's angle 2 theta, intensity and relative intensity (expressed as a percentage of the most intense ray):

| Angle 2 theta (°) | Inter-planar distance d (Å) | Intensity | Relative intensity (%) |
|---|---|---|---|
| 5.169 | 17.08 | 523 | 16.5 |
| 8.379 | 10.54 | 1001 | 31.5 |
| 9.350 | 9.45 | 3175 | 100 |
| 14.746 | 6.00 | 236 | 7.4 |
| 15.411 | 5.74 | 753 | 23.7 |
| 15.931 | 5.56 | 279 | 8.8 |
| 16.711 | 5.30 | 113 | 3.6 |
| 18.161 | 4.88 | 122 | 3.8 |
| 20.564 | 4.32 | 1198 | 37.7 |
| 21.285 | 4.17 | 330 | 10.4 |
| 21.781 | 4.08 | 317 | 10 |
| 22.632 | 3.93 | 190 | 6 |
| 23.308 | 3.81 | 133 | 4.2 |
| 23.797 | 3.74 | 427 | 13.4 |
| 24.276 | 3.66 | 118 | 3.7 |
| 25.190 | 3.53 | 92 | 2.9 |
| 25.924 | 3.43 | 251 | 7.9 |
| 26.646 | 3.34 | 250 | 7.9 |
| 27.620 | 3.23 | 96 | 3 |
| 28.306 | 3.15 | 133 | 4.2 |

The invention relates also to a process for the preparation of the β crystalline form of the compound of formula (I), which process is characterized in that:

either, according to a first embodiment, a solution of perindopril tert-butylamine salt in dichloromethane is heated at reflux and is then rapdily cooled to 0° C. and the solid obtained is collected by filtration, or, according to a second embodiment, a solution of perindopril tert-butylamine salt in ethyl acetate is heated at reflux and is then rapidly cooled to 5° C. and the solid obtained is collected by filtration.

In the crystallisation process according to the invention it is possible to use the compound of formula (I) obtained by any process. Advantageously, the compound of formula (I) obtained by the preparation process described in patent specification EP 0 308 341 is used.

In the first embodiment of the process according to the invention, the concentration of the compound of formula (I) in the dichloromethane is preferably from 100 to 200 g/liter.

In the second embodiment of the process according to the invention, the concentration of the compound of formula (I) in the ethyl acetate is preferably from 70 to 90 g/liter.

The invention relates also to pharmaceutical compositions comprising as active ingredient the β crystalline form of the compound of formula (I) together with one or more appropriate, inert, non-toxic excipients. Among the pharmaceutical compositions according to the invention, there may be mentioned more especially those that are suitable for oral, parenteral (intravenous or subcutaneous) or nasal administration, tablets or dragées, sublingual tablets, gelatin capsules, lozenges, suppositories, creams, ointments, dermal gels, injectable preparations, drinkable suspensions etc.

The useful dosage can be varied according to the nature and severity of the disorder, the administration route and the age and weight of the patient. It varies from 1 to 500 mg per day in one or more administrations.

The pharmaceutical compositions according to the invention may also comprise a diuretic such as indapamide.

The following Examples illustrate the invention but do not limit it in any way.

The powder X-ray diffraction spectrum was measured under the following experimental conditions:
Siemens D5005 diffractometer, scintillation detector,
copper anticathode ($\lambda=1.5405$ Å), voltage 40 kV, intensity 40 mA,
mounting $\theta$-$\theta$,
measurement range: 5° to 30°,
increment between each measurement: 0.02°,
measurement time per step: 2 s,
variable slits : v6,
filter K$\beta$ (Ni),
no internal reference,
zeroing procedure with the Siemens slits,
experimental data processed using EVA software (version 5.0).

EXAMPLE 1

β Crystalline Form of Perindopril Tert-butylamine Salt 135 g of perindopril tert-butylamine salt obtained according to the process described in patent specification EP 0 308 341 are dissolved in 1100 ml of dichloromethane heated at reflux.

The solution is then cooled to 0° C. and the solid obtained is collected by filtration.

Powder X-ray Diffraction Diagram:

The powder X-ray diffraction profile (diffraction angles) of the β form of perindopril tert-butylamine salt is given by the significant rays collated in the following table together with the intensity and relative intensity (expressed as a percentage of the most intense ray):

| Angle 2 theta (°) | Inter-planar distance d (Å) | Intensity | Relative intensity (%) |
|---|---|---|---|
| 5.169 | 17.08 | 523 | 16.5 |
| 8.379 | 10.54 | 1001 | 31.5 |
| 9.350 | 9.45 | 3175 | 100 |
| 14.746 | 6.00 | 236 | 7.4 |
| 15.411 | 5.74 | 753 | 23.7 |
| 15.931 | 5.56 | 279 | 8.8 |
| 16.711 | 5.30 | 113 | 3.6 |
| 18.161 | 4.88 | 122 | 3.8 |
| 20.564 | 4.32 | 1198 | 37.7 |
| 21.285 | 4.17 | 330 | 10.4 |
| 21.781 | 4.08 | 317 | 10 |
| 22.632 | 3.93 | 190 | 6 |
| 23.308 | 3.81 | 133 | 4.2 |
| 23.797 | 3.74 | 427 | 13.4 |
| 24.276 | 3.66 | 118 | 3.7 |
| 25.190 | 3.53 | 92 | 2.9 |
| 25.924 | 3.43 | 251 | 7.9 |
| 26.646 | 3.34 | 250 | 7.9 |
| 27.620 | 3.23 | 96 | 3 |
| 28.306 | 3.15 | 133 | 4.2 |

EXAMPLE 2

β Crystalline Form of Perindopril Tert-butylamine Salt 125 g of perindopril tert-butylamine salt obtained according to the process described in patent specification EP 0 308 341 are dissolved in 1.5 liters of ethyl acetate heated at reflux.

The solution is then cooled rapidly to 5° C. and the solid obtained is collected by filtration.

EXAMPLE 3

Pharmaceutical Composition

Preparation formula for 1000 tablets each containing 4 mg of active ingredient:

| | |
|---|---|
| Compound of Example 1 | 4 g |
| Hydroxypropylcellulose | 2 g |
| Wheat starch | 10 g |
| Lactose | 100 g |
| Magnesium stearate | 3 g |
| Talc | 3 g |

We claim:

1. A β crystalline form of the compound of formula (I):

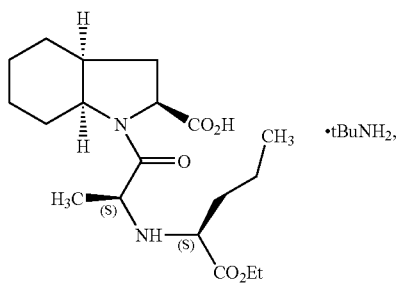

(I)

exhibiting essentially the following powder X-ray diffraction data, measured using a diffractometer (copper anticathode) and expressed in terms of inter-planar distance d and Bragg's angle 2 theta:

| Angle 2 theta (°) | Inter-planar distance d (Å) |
|---|---|
| 5.169 | 17.08 |
| 8.379 | 10.54 |
| 9.350 | 9.45 |
| 14.746 | 6.00 |
| 15.411 | 5.74 |
| 15.931 | 5.56 |
| 16.711 | 5.30 |
| 18.161 | 4.88 |
| 20.564 | 4.32 |
| 21.285 | 4.17 |
| 21.781 | 4.08 |
| 22.632 | 3.93 |
| 23.308 | 3.81 |
| 23.797 | 3.74 |
| 24.276 | 3.66 |
| 25.190 | 3.53 |
| 25.924 | 3.43 |
| 26.646 | 3.34 |
| 27.620 | 3.23 |
| 28.306 | 3.15. |

* * * * *